United States Patent
Sweeney

(10) Patent No.: US 7,316,898 B2
(45) Date of Patent: Jan. 8, 2008

(54) METHOD OF DETERMINING ADENOVIRUS PARTICLE CONCENTRATION

(75) Inventor: Joyce A. Sweeney, Collegeville, PA (US)

(73) Assignee: Merck & Co., Inc., Rahway, NJ (US)

( * ) Notice: Subject to any disclaimer, the term of this patent is extended or adjusted under 35 U.S.C. 154(b) by 454 days.

(21) Appl. No.: 10/505,026

(22) PCT Filed: Feb. 14, 2003

(86) PCT No.: PCT/US03/04564

§ 371 (c)(1),
(2), (4) Date: Aug. 16, 2004

(87) PCT Pub. No.: WO03/070891

PCT Pub. Date: Aug. 28, 2003

(65) Prior Publication Data

US 2005/0095580 A1    May 5, 2005

Related U.S. Application Data

(60) Provisional application No. 60/358,331, filed on Feb. 20, 2002.

(51) Int. Cl.
- C12Q 1/68 (2006.01)
- C12Q 1/70 (2006.01)
- C12Q 15/861 (2006.01)
- C12N 7/01 (2006.01)
- A61K 48/00 (2006.01)

(52) U.S. Cl. ............... 435/5; 435/6; 435/235.1; 435/320.1

(58) Field of Classification Search ............... None
See application file for complete search history.

(56) References Cited

U.S. PATENT DOCUMENTS 5,585,362 A   12/1996  Wilson et al.
5,837,520 A   11/1998  Shrabram et al.
6,033,908 A    3/2000  Bout et al.
6,194,191 B1   2/2001  Zhang et al.
6,316,185 B1  11/2001  Saifer et al.

OTHER PUBLICATIONS

Lawrence et al., "Intracellular Uncoating of Type 5 Adenovirus Deoxyribonucleic Acid", Journal of Virology, Vol. 1, pp. 851-867, Oct. 1967.

Maizei et al., The Polypeptides of Adenovirus, Virology, vol. 36, pp. 115-125, 1968.

Liebermann et al., "Quantification of adenovirus particles", Journal of Virological Methods, vol. 50, pp. 281-292, 1994.

Huyghe et al., "Purification of a Type 5 Recombinant Adenovirus Encoding Human p53 by Column Chromatography", Human Gene Therapy, vol. 6, pp. 1403-1416, Nov. 1995.

Mittereder et al., "Evaluation of the Concentration and Bioactivity of Adenovirus Vectors for Gene Therapy", Journal of Virology, vol. 70, pp. 7498-7509, Nov. 1996.

*Primary Examiner*—David Guzo
(74) *Attorney, Agent, or Firm*—Henry P. Wu; Sheldon O. Heber

(57) ABSTRACT

The invention discloses a simple, accurate and reproducible method of determining viral particle concentration, especially for any serotype of adenovirus. More specifically, an accurate absorptivity/extinction coefficient in units of viral particles per milliliter per absorbance unit per centimeter (vp/mL-AU-cm) for a sample virus, such as adenovirus, at 260 nanometers (nm) is disclosed, as well as an ultraviolet (UV) absorbance method to determine virus particle concentrations based on this established absorptivity/extinction coefficient and absorbances at 260 nm for purified virus preparations, such as adenovirus preparations.

9 Claims, 2 Drawing Sheets

METHOD OF DETERMINING ADENOVIRUS PARTICLE CONCENTRATION

CROSS-REFERENCE TO RELATED APPLICATIONS

This application claims benefit under 35 U.S.C. § 119(e), to U.S. provisional application 60/358,331 filed Feb. 20, 2002.

STATEMENT REGARDING FEDERALLY-SPONSORED R&D

Not Applicable

REFERENCE TO MICROFICHE APPENDIX

Not applicable.

FIELD OF THE INVENTION

The present invention relates to an improved method for determining virus particle concentration in a virus preparation. The methods disclosed herein provide for a simple, accurate and reproducible method to determine viral particle concentration using 260 nm absorbance. This methodology is especially applicable to spectrophotometric measurement of adenovirus particle concentration. The methods of the present invention ensures complete disruption of virus particles and viral DNA conformation prior to absorbance measurements, therefore eliminating absorbance measurement errors due to light scattering interferences and hyperchromic shift, and thus providing an extinction coefficient at 260 nm that is directly related to protein concentration. This methodology reduces inter-laboratory variability in determining viral particle concentrations, especially adenovirus particle concentrations.

BACKGROUND OF THE INVENTION

The introduction of adenovirus as a vector for in vivo delivery of transfected genes used in therapeutic treatments, as well as in vaccines, has resulted in a realm of highly focused research and development that will ultimately be applied to many different disease targets. Clinical studies used to estimate dosage levels of transfected adenovirus particles for appropriate efficacy are highly dependent upon techniques that can provide accurate and reproducible methods to assess viral particle concentration. Several methods for determining adenovirus particle concentration using spectroscopic methods with various types of sample pretreatments have been published in the literature (see. e.g., Lawrence and Ginsberg, 1967, *J. Virol.* 1: 851-867; Maizel et al., 1968, *Virology* 36: 115-125; Liebermann and Mentel, 1994, *J. Virological Methods* 50, 281-292; Huyghe et al., 1995, *Hunan Gene Therapy* 6, 1403-1416; Mittereder et al., 1996, *J. Virol.* 70 (11), 7498-7509; Shabram et al., 1997, *Human Gene Therapy* 8, 453-465). Maizel et al. (id.) in particular established a correlation between protein content of adenovirus preparations and absorbance at 260 nm and reported an absorptivity for purified adenovirus preparations of $1.1 \times 10^{12}$ viral particles per absorbance unit (AU). This method and absorptivity value have been cited extensively in the literature as the basis for quantitating adenovirus particle concentration. However, while the simplicity of this spectroscopic method is attractive, application of this methodology has resulted in poor accuracy when compared to direct evaluation of protein concentration, and higher than expected intra- and inter-assay variability than would be expected from a spectroscopic method. No one method, including the methodology forwarded by Maizel et al. (id.) has been applied in a consistent enough manner to provide a "universal" approach for defining adenovirus concentration. Furthermore, many of these methods produce conflicting results. In fact, Mittereder et al. (1996, *J. Virol.* 70 (11), 7498-7509) state in a work intended to evaluate concentration and bioactivity of adenovirus, that the accuracy of the absorptivity of adenovirus preparations at 260 nm is an area that needs to be further investigated. It would be desirable to have at hand a simple, precise and reproducible method for determining virus particle concentrations, especially viral particles which are being utilized in gene therapy and/or gene vaccination regimes, such as a representative recombinant adenovirus vector. The present invention addresses and meets these needs by disclosing a simple, precise and easily reproducible method for determining viral particle concentration using spectroscopic methods.

SUMMARY OF THE INVENTION

The present invention relates to a simple, accurate and reproducible method of determining viral particle concentration by UV spectrophotometry, especially for any serotype of adenovirus. More specifically, an accurate absorptivity/extinction coefficient in units of viral particles per milliliter per absorbance unit per centimeter (vp/mL-AU-cm) for a sample virus, such as adenovirus, at 260 nanometers (nm) is disclosed, as well as an ultraviolet (UV) absorbance method to determine virus particle concentrations based on this established absorptivity/extinction coefficient and absorbances at 260 nm for purified virus preparations, such as adenovirus preparations. A preferred sample virus is any adenovirus wherein an initial calculation of the molecular weight of DNA is known, thus allowing for a series of simple mathematical calculations as described herein.

To this end, the present invention relates in part to a improved method of determining the virus particle concentration of a virus preparation from a UV absorbance measurement which comprises calculating the absorptivity/extinction coefficient ($\epsilon_{260}$) for the respective serotype of the virus preparation, measuring the $A_{260}$ of a sample from the virus preparation, and determining viral particle concentration of said viral sample from the $\epsilon_{260}$ and $A_{260}$ measurements. As noted above, a preferred virus is any serotype of adenovirus while especially preferred serotypes include Ad5, Ad2, Ad24, Ad31, Ad4, Ad12, Ad6, Ad17, Ad33, Ad42, and Ad16. It should be possible to practice this improved methodology on any adenovirus sample wherein the molecular weight of the Ad genome can be calculated. Therefore, any Ad of which the genome has previously been subjected to DNA sequencing is amenable to the methodology of the present invention.

The present invention also relates to a method of calculating the absorptivity/extinction coefficient ($\epsilon_{260}$) for a virus serotype such that derivation of this constant allows for future UV-based methods (such as those disclosed herein) to determine particle concentration for the respective virus, with such methods being simple, accurate and reproducible. A method of calculating the ($\epsilon_{260}$) for a virus serotype comprises an initial determination of the viral particle concentration of a sample from a virus preparation of a virus serotype, treating an independent sample from said virus preparation under conditions which result in complete disruption of viral particles and complete disruption of virus DNA conformation, determining the $A_{260}$ of the independent sample and correlating the initial viral particle concentration with the $A_{260}$ value. It is disclosed herein that accurate calculation of $\epsilon_{260}$ for a virus serotype requires treatment conditions that result in complete disruption of virus particles and complete disruption of virus DNA conformation. A preferred application of this methodology would involve calculation of ($\epsilon_{260}$) for any serotype of adenovirus while being especially preferred for serotypes which include Ad5, Ad2, Ad24, Ad31, Ad4, Ad12, Ad6, Ad17, Ad33, Ad42, and Ad16.

As used herein, "Ad" refers to—adenovirus—.

As used herein, "UV" refers to—ultraviolet—.

As used herein, "$\epsilon_{260}$" refers to—absorptivity/extinction coefficient in units of viral particles per milliliter per absorbance unit per centimeter (vp/mL-AU-cm) at 260 nm—.

As used herein, "SDS" refers to—sodium dodecyl sulfate—.

DETAILED DESCRIPTION OF THE INVENTION

Figure 1:
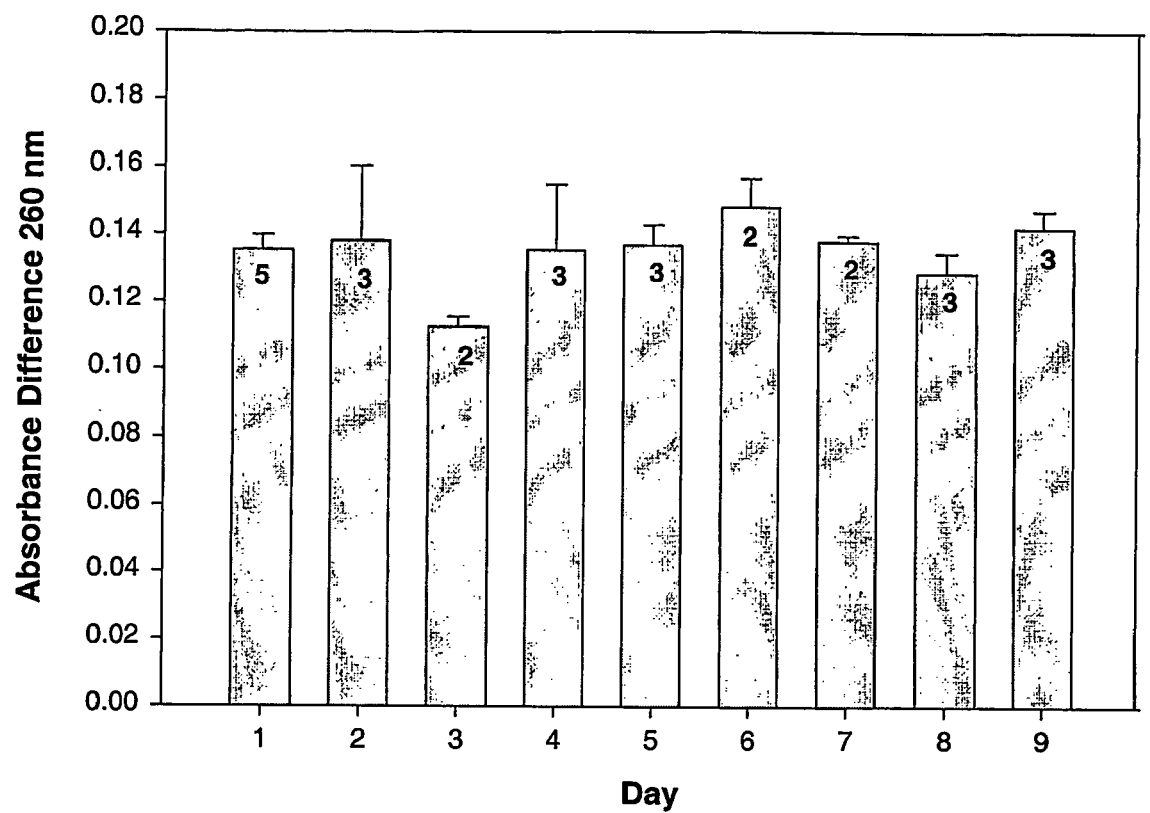
FIG. 1 shows absorbance difference data at 260 nm derived from 26 individual analyses of an adenovirus control lot displayed as within-day averages for various replicate analyses per day. Within-day standard deviations are shown by the error bars; replicates analyzed per day are also listed.

The present invention relates to a spectroscopic method of determining virus particle concentration in a respective virus preparation.

The present invention also relates to a spectroscopic method of determining adenovirus particle concentration in a respective adenovirus preparation. The essence of the present invention centers around an improved method of determining virus particle concentration (exemplified herein with an Ad5 serotype) in a sample where residual host cell nucleic acids and other potential contaminating materials are at or below a concentration that would influence the measurement of adenovirus particles within a respective sample. The exemplified adenovirus preparations subjected to this improved methodology exhibited $A_{260}/A_{280}$ absorbance ratios ranging from 1.23 to 1.33, showing a reasonably consistent nucleic acid/protein ratios in these preparations. It will be evident upon review of this specification that a viral preparation which is useful to practice the present invention is a virus preparation which has been reasonably purified away from host nucleic acids and other host contaminants such that the respective virus preparation is amenable to the methodology disclosed herein.

To this end, the present invention specifically relates to a simple, precise, rugged and reproducible ultraviolet (UV) absorbance method to assess adenovirus particle concentration which is based on establishment of several requirements: (1) accurate evaluation of viral mass, such as by direct quantitation of virus protein content; (2) as noted supra, evidence of compositional consistency between preparations to be evaluated with regard to those elements that significantly impact the measurement; and, (3) assurance that the analytical method will result in equal and consistent evaluation of all samples. It is known in the art, as forwarded by Maizel et al. (1968, Virology 36: 115-125) that a correlation exists between protein content of adenovirus preparations and absorbance at 260 nm, leading to a report that the absorptivity ($\epsilon_{260}$ value) for purified adenovirus preparations is $1.1 \times 10^{12}$ viral particles per absorbance unit (AU). This method and absorptivity value have been cited extensively in the literature as the basis for quantitating adenovirus particle concentration. While the simplicity of this spectroscopic method is attractive, application of this information may result in poor accuracy when compared to direct evaluation of protein concentration. Further investigations revealed that the prescribed sample treatment method used to prepare adenovirus preparations for spectroscopic evaluation was inadequate to ensure consistent disruption of the virus particles and complete unfolding of the viral DNA. This led, in turn, to variable contributions to the 260 nm absorbance measurements from (1) the variable degrees of hyperchromism associated with variable amounts of random coil DNA relative to helical DNA and (2) to a lesser degree from scattered light caused by remnant virus particles. The magnitude of the hyperchromic effect, which is exhibited as an increase in absorbance at 260 nm, is related to the degree of DNA disruption (e.g., see Tinoco, 1959, J. Amer. Chem. Soc. 82, 4785-4790; Rhodes, 1961, J. Amer. Chem. Soc. 83, 3609-3617; and Painter and Koenig, 1976, Biopolymers 15, 241-255). Moreover, since Maizel's factor is apparently derived from adenovirus that is not completely disrupted prior to absorbance measurement, and the incubation period is very loosely defined (i.e., overnight), there is likely to be difficulty in achieving consistent DNA disruption between experiments and between laboratories using the same methods. Thus, the factor that Maizel empirically derived, may not be applicable to other experiments in which the DNA is disrupted to a different degree or, as preferable, to a degree of complete disruption.

The present invention encompasses advances in two related areas which result in the ability to incorporate this disclosed methodology, now with the confidence that simplicity parallels both accuracy and reproducibility in determining viral particle concentration. Namely, the present invention shows in part the following: (1) determination of an accurate absorptivity/extinction coefficient for adenovirus at 260 nm for a given set of experimental conditions wherein the absorptivity/extinction coefficient for adenovirus at 260 nm under conditions of complete DNA conformational disruption is disclosed herein to be $1.8 \times 10^{12}$ vp/mL-AU-cm; and, (2) the establishment of experimental sample pre-treatment conditions that will result in not only complete viral particle disruption to avoid light scattering interferences, but just as importantly, complete disruption of DNA conformation to permit accurate and precise determinations of viral particle concentrations of purified adenovirus preparations from absorbance measurements at 260 run, using the previously established absorptivity/extinction coefficient established under the same sample pre-treatment conditions as noted in (1). The exemplified pre-treatment conditions for Ad5 virus was incubation in 1% sodium dodecyl sulfate (SDS) at 100° C. for 4 minutes. Example 1 discloses the accurate determination of $E_{260}$ value derived for an Ad5/Ad2-related adenovirus. It will be evident upon review of this specification that alternative pre-treatment conditions may be utilized by the skilled artisan which results in both a complete viral particle and DNA conformation disruptions. Such alternatives may be utilized for various adenovirus serotypes as well as other viruses, so as to allow for both calculation of (i) an accurate $\epsilon_{260}$ value and (ii) for general pre-treatment conditions for measuring viral particle concentration.

As noted supra, Maizel et al. (1968, *Virology* 36: 115-125) demonstrated that adenovirus particle concentration can be determined by measurement of adenovirus ultraviolet (UV) absorbance at 260 nm using a previously established adenovirus 260 nm absorptivity/extinction coefficient. The 260 nm absorbance measurement of adenovirus solution requires a sample pre-treatment with sodium dodecyl sulfate (SDS) to disrupt the viral particles in order to minimize/eliminate the interference effects of light scattering from the particles which leads to falsely elevated absorbance measurements. Determination of the absorptivity/extinction coefficient involves determination of the viral particle concentration by a completely independent method, and correlating that concentration to an absorbance measurement at 260 nm for the same adenovirus solution and normalizing the ratio to one absorbance unit (AU) in a one centimeter (cm) path length optical cell. As exemplified herein, an initial step involved calculation of adenovirus particle concentration by the Lowry Protein method. Also, this independent method for establishment of the viral particle concentration involves determining the protein concentration in units of protein mass per volume and converting the protein concentration to viral particles per volume using the protein mass per virion which is calculated based on information provided by Green and Pina (id.) (i.e., DNA molecular weight of adenovirus is $2.3 \times 10^7$ and the fact that DNA is considered to comprise 13% of the dry weight viral mass). The molecular weight of the respective adenovirus will be known (e.g., for Ad2, see Green and Pina; (id.) or calculate the MW from the known genomic DNA sequence, such as GenBank Accession No. NC001405), wherein molecular weight of viral DNA=$2.3 \times 10^7$ g/mole. Since DNA is 13% of the adenovirus virion dry weight, $$TotalVirionMW = \frac{2.3 \times 10^7 \text{ g/mole}}{0.13} = 1.77 \times 10^8 \text{ g/mole}$$

Also, Adenovirus serotypes consist only of DNA and protein, and protein will comprise 87% of virion:

MW viral protein=$0.87(1.77 \times 10^8)$=$1.54 \times 10^8$ g/mole

Since Protein mass per viral particle=MW viral protein divided by Avogadro's No.:

$$\text{protein mass/virion} = \frac{1.54 \times 10^8 \text{ g/mole}}{6.023 \times 10^{23} \text{ vp/mole}} = 2.56 \times 10^{-10} \text{ μg protein/vp}$$

Vial particle concentration (vp/mL) of a preparation can be calculated from the experimentally determined protein concentration and the above factor for Protein mass/vp as follows:

Viral Particle Conc. (vp/mL)=Protein Conc. (μg/mL)/
$2.56 \times 10^{-10}$ (μg protein/virion)

Subsequently, the adenovirus absorptivity/extinction coefficient can be calculated so long as the following parameters are determined: (1) adenovirus sample of known viral particle concentration, such as that determined by Lowry Protein analysis; and (2) 260 m Absorbance measurements of Adenovirus sample in item 1 and matrix blank, both equivalently SDS-treated/diluted.

$$\varepsilon_{260} = \frac{C_L}{(\Delta A)_{260}(F)(b)}$$

where,
$C_L$ is the viral particle concentration in units of vp/mL derived from Lowry protein analysis
$\Delta A A_{260}$ is the absorbance difference of test sample minus matrix blank at 260 nm
F is the sample dilution factor used to obtain the absorbance measurement
b is the path length of the sample cuvette, in this case, 1 cm For Adenovirus (such as a Group C serotype and any other with similar DNA base pair number)

$$\varepsilon_{260} = \frac{4.9 \times 10^{11} \text{ vp/mL}}{(0.1352 \text{ AU})(2)(1 \text{ cm})} = 1.8 \times 10^{12} \text{ vp/mL-AU-cm}$$

Finally, to calculate viral particle concentration from 260 nm absorbance and $\epsilon_{260}$, the following are required: (1) previously established Adenovirus $\epsilon_{260}$, and (2) 260 nm absorbance measurement of SDS-treated Adenovirus test sample and matrix blank $C_{A260} = \Delta A_{260} \times F \times b \times \epsilon_{260}$ where,
$C_{A260}$ is the viral particle concentration derived from absorbance at 260 nm
$\Delta A_{260}$ is the absorbance difference of test sample minus matrix blank at 260 nm (i.e., $A_{260test} - A_{260blank}$)
F is the sample dilution factor used to obtain the absorbance measurement
B is the cell pathlength in cm
$\epsilon_{260}$ is the absorptivity of adenovirus at 260 nm in units of vp/mL-AU-cm One aspect of the invention is the disclosure that an SDS sample pre-treatment not only disrupts the intact viral particle shell, but will also disrupt the conformation of the viral DNA, causing the DNA to display a hyperchromic effect (increase in absorbance at specific wavelengths) upon disruption from an alpha-helical conformation to a random coil conformation. The hyperchromic effect was not considered in Maizel et al. (id.). Further, the degree of the hyperchromic effect is related to the degree of DNA disruption. Therefore, as shown herein, experimental conditions must be critically defined with regard to SDS concentration (or any other alternative compound which results in a complete disruption of both virus and viral DNA) and incubation time prior to absorbance measurement in order to obtain reproducible degrees of DNA disruption that will thus generate consistent absorbance measurements. Ideally, conditions that result in complete DNA disruption should generate the most consistent absorbance measurements. The Maizel et al. (id.) disclosure presents several issues, namely (i) conditions are very loosely defined (e.g., "overnight incubation at room temperature", rather than a specific incubation time period and conflicting SDS concentrations of 0.5% versus 1.0%). The degree of DNA disruption can vary depending upon how these directions are interpreted; (ii) 0.5% SDS with overnight incubation was reported not to be sufficient for complete disruption of viral proteins as confirmed by protein gel electrophoresis studies; and (iii) the absorptivity factor is reported in units of absolute viral particles per absorbance unit: one might assume this value to be in units of vp/mL-AU-cm, which may or may not be a correct assumption.

Thus, a central portion of the present invention is to provide an accurate 260 nm viral absorptivity/extinction coefficient generated using sample pre-treatment conditions that provide complete disruption of the virus DNA conformation, thus permitting accurate and reproducible determinations of the virus particle concentrations on purified virus preparations by a simple and robust technique. This methodology is disclosed in detail supra and exemplified in Example 1, disclosing a consistent and reproducible method for determining adenovirus particle concentration. These results are based on extensive spectroscopic analyses, including a rugged sample preparation method, and rigorous determinations of protein concentration. Subsequent application of this methodology to several purified adenovirus preparations produced spectroscopic determinations of virus particle concentration that correlate extremely well with independent protein concentration measurements, confirming an assay precision of ±10% (one relative standard deviation, RSD). Overall, the method reported here provides a simple, robust and rugged approach for defining adenovirus particle concentration that produces a more accurate and precise result than previously established methods.

The following non-limiting Examples are presented to better illustrate the invention.

EXAMPLE 1

Determination of Ad5 Concentration for Purified Ad 5 Preparations

Materials and Methods—Purified serotype 5 adenovirus preparations were provided by Merck Research Laboratories, Fermentation and Cell Culture Department and Vaccine Bioprocess Engineering Department. Only purified adenovirus preparations with an $A_{260}/A_{280}$ absorbance ratio of 1.2 to 1.3 were included in this study. Adenoviral vectors such as those utilized to exemplify the methodology of the present invention can be constructed using known techniques, such as those reviewed in Hitt et al. (1997, "Human Adenovirus Vectors for Gene Transfer into Mammalian Cells" *Advances in Pharmacology* 40:137-206), which is hereby incorporated by reference. In constructing such an adenoviral vector, it is often convenient to insert them into a plasmid or shuttle vector. These techniques are known and described in Hitt et al., supra. The adenoviral essentially contains adenoviral sequences (with non-functional or deleted E1 and E3 regions) and a gene expression cassette (e.g., HIV p55 gag) flanked by convenient restriction sites. The plasmid portion of the shuttle vector often contains an antibiotic resistance marker under transcriptional control of a prokaryotic promoter so that expression of the antibiotic does not occur in eukaryotic cells. Ampicillin resistance genes, neomycin resistance genes and other pharmaceutically acceptable antibiotic resistance markers may be used. To aid in the high level production of the polynucleotide by fermentation in prokaryotic organisms, it is advantageous for the shuttle vector to contain a prokaryotic origin of replication and be of high copy number. A number of commercially available prokaryotic cloning vectors provide these benefits. It is desirable to remove non-essential DNA sequences. It is also desirable that the vectors not be able to replicate in eukaryotic cells. This minimizes the risk of integration of polynucleotide vaccine sequences into the recipients' genome. Tissue-specific promoters or enhancers may be used whenever it is desirable to limit expression of the polynucleotide to a particular tissue type. Viral vectors can be propagated in various E1 complementing cell lines, including the known cell lines 293 and PER.C6®. Both these cell lines express the adenoviral E1 gene product. PER.C6® is described in WO 97/00326 (published Jan. 3, 1997) and issued U.S. Pat. No. 6,033,908, both of which are hereby incorporated by reference. It is a primary human retinoblast cell line transduced with an E1 gene segment that complements the production of replication deficient (FG) adenovirus, but is designed to prevent generation of replication competent adenovirus by homologous recombination. Cells of particular interest have been stably transformed with a transgene that encodes the AD5E1A and E1B gene, like PER.C6™, from 459 bp to 3510 bp inclusive. 293 cells are described in Graham et al. (1977, *J. Gen. Virol* 36:59-72), which is hereby incorporated by reference. Propagated viral vectors may be purified through any process known in the art which will result in a sample where residual host cell nucleic acids and other potential contaminating materials are at or below a concentration that would influence the measurement of adenovirus particles within a respective sample (e.g., see Huyghe et al., 1995, *Human Gene Therapy* 6, 1403-1416; and U.S. Pat. No. 6,194,191, issued to Zhang et al. on Feb. 27, 2001, both references which are hereby incorporated by reference).

Protein concentration—Protein concentrations of adenovirus samples were determined by the method of Lowry (1951, *J. Biol. Chem.* 193, 265-275) calibrated with bovine serum albumin (BSA) standards from either NIST or Pierce Chemical Company. Protein content per virion was calculated to be $2.56 \times 10^{-10}$ µg protein/vp based on previously established viral DNA molecular weight of $2.3 \times 10^7$ g DNA/mole virus with viral DNA content comprising 13% of virion dry weight for adenovirus serotype 2 (Green et al., 1967, *Proc. Natl. Acad. Sci. U.S.* 57, 1302-1309; Green and Piña, 1964, *Proc. Natl. Acad. Sci. U.S.* 51, 1251-1259; Green and Piña, 1963, *Virology* 20, 199-207). The adenovirus serotype 5 gene sequence is 99.4% homologous with the adenovirus serotype 2 gene sequence (Green et al., 1979, *Virology* 93, 481-492), thus showing the relevance of these calculations for the Ad5 example herein. Viral particle concentrations were calculated from protein concentrations by dividing experimentally derived protein concentrations by the constant of $2.56 \times 10^{-10}$ µg protein per virion. All protein assays included BSA calibration standards over the range of 2.8 to 20 µg BSA and a reference preparation of purified adenovirus.

Absorbance measurements—Absorbance measurements of adenovirus samples at 260 nm were acquired using a Beckman diode array spectrophotometer set to zero absorbance with a water background. Sub-micro quartz cuvettes (Starna Cells) with a sample volume of 40 µL and a pathlength of 1 cm were used for absorbance measurements. The same cuvette was used to measure samples and blanks. Test samples were brought to 1.0% (w/v) sodium dodecyl sulfate (SDS), tightly capped, and incubated in a heating block at 100° C.±1° C. for 4 minutes. After incubation, samples were cooled to room temperature and thoroughly mixed by a minimum of five inversion and vortex cycles prior to the absorbance measurements. Blank samples containing the test sample matrix without adenovirus were treated in the same manner to account for excipient and reagent contributions to the absorbance at 260 nm. Since unexpected leaching of UV absorbing species from polypropylene tubes was observed with varying degrees depending upon tube manufacturer, it is recommended, and hence preferred, that the incubations be performed in glass tubes. Any absorbance due to leaching was subtracted from the test sample via the blank measurement. While the accuracy of the absorbance difference seemed to be unaffected by the leaching problem, the precision was slightly impacted.

In order to maintain an acceptable level of accuracy and precision in the assay, only absorbance differences between test samples and matrix blanks of greater than 0.05 absorbance units (AU) were used. Also, to ensure that absorbance measurements were linear within the limits of the instrumentation and Beer's Law, only absorbance measurements of less than 1 AU were considered acceptable. If an absorbance value of greater than 1 AU was observed for the test samples, the entire measurement, including sample pre-treatment was repeated using an appropriate dilution of the original test sample; matrix blanks with components described above typically had absorbance values less than 0.1 AU. The individual recording of test sample and matrix blank absorbance measurements served to isolate any variability associated with test sample from that associated with instrumental variability.

Results and Discussion—Protein Concentration Assay—Protein concentration analysis was performed seven times over a period of six months using a single reference preparation (lot A) of purified adenovirus. The results are summarized in Table 1. Viral particle concentrations (vp/mL) were calculated from the protein concentration measurements as follows: Molecular Weight (MW) viral DNA=2.3× $10^7$ g/mole virus (Green et al., 1967, id.), and DNA is 13% of virion dry weight (Green and Piña, 1964, id.). Therefore, MW of viral particle=1.76×$10^8$ g/mole virus and MW viral protein=1.54×$10^8$ g/mole; Protein mass per viral particle=MW viral protein/Avogadro's No.=2.56×$10^{-10}$ μg protein/viral particle; Viral Particle Concentration=Protein Concentration/Protein mass per viral particle. Overall, the results are very consistent, providing a viral particle concentration for this lot of 4.9×$10^{11}$ vp/mL (based on protein concentration) with an RSD of 2.8%.

TABLE 1

Summary of protein concentration assay results and calculated viral particle concentration data from replicate analysis of a single control preparation (lot A) of purified adenovirus

| Test Run | Protein Concentration (ug/mL) | Viral Particle Concentration (×$10^{11}$ vp/mL) |
|---|---|---|
| 1 | 124 | 4.8 |
| 2 | 125 | 4.9 |
| 3 | 125 | 4.9 |
| 4 | 127 | 5.0 |
| 5 | 119 | 4.7 |
| 6 | 128 | 5.0 |
| 7 | 130 | 5.1 |
| AVERAGE | 125.6 | 4.9 |
| STD DEV | 3.5 | 0.14 |
| % RSD | 2.8% | 2.8% |

UV Absorbance. The eleven purified adenovirus preparations used in this study exhibited $A_{260}/A_{280}$ absorbance ratios ranging from 1.23 to 1.33 (see Table 2), reflecting a reasonably consistent nucleic acid to protein ratio in these preparations with residual host cell nucleic acids well below the level that would influence these analyses. As such, use of the adenovirus 260 nm absorptivity generated here is relatively intensive to the purity of the product.

TABLE 2

Viral particle concentration results for eleven purified adenovirus preparations as determined by protein concentration analysis (column 3) and UV absorbance using the modified method and $\epsilon_{260}$ value of 1.8 ×$10^{12}$ virus particles/mL-AU-cm (column 4).

| | Ratio | Virus Particle Concentration (× $10^{11}$ vp/mL) | |
|---|---|---|---|
| Adenovirus Lot | $A_{260}/A_{280}$ | Protein Assay | Modified UV Assay |
| A | 1.33 | 4.9 | 4.9 |
| B | 1.27 | 78.1 | 81.7 |
| C | 1.28 | 2.7 | 3.0 |
| D | 1.29 | 3.2 | 3.5 |
| E | 1.23 | 4.5 | 5.3 |
| F | 1.28 | 4.5 | 5.0 |
| G | 1.29 | 6.7 | 7.4 |
| H | 1.28 | 6.5 | 7.2 |
| I | 1.27 | 6.7 | 7.8 |
| J | 1.29 | 4.6 | 4.3 |
| K | 1.26 | 14.3 | 15.2 |

The absorbance difference data at 260 nm between test sample and blank were generated for the control preparation (lot A) of purified adenovirus in order to establish an absorptivity value at 260 nm ($\epsilon_{260}$). Absorbance differences for this single preparation were acquired in 26 separate analyses on nine different days throughout a seven month period to provide insights on assay variability and ruggedness. These absorbance measurements were obtained using a two-fold dilution of the purified adenovirus sample with SDS pre-treatment as described above. FIG. 1 shows the nine daily averages and standard deviations for the 260 nm absorbance difference data, $\Delta A_{260}$ (i.e., $A_{260-test}$ minus $A_{260-blank}$) along with the number of analyses per day. The results suggest that multiple preparations should be tested to obtain an accurate result, as occasional individual results were shown to differ by up to 15% from the global average, whereas, typically the average of any three proximate analyses differed by about 5%. The overall similarity of the within day and between day variability suggests that the occasionally high variability observed in two of the replicate analyses was likely associated with pipetting variability and/or differential evaporation of the small volume samples during the heating/cooling cycle of the sample treatment. The latter situation can be eliminated by ensuring that the sample tubes are capped tightly during the pre-treatment incubation and mixed thoroughly by inversion and vortex after cooling to room temperature, post-incubation. In any event, by performing triplicate analyses of any given sample on the same day or on different days, the average result would be expected to have a (RSD) on the order of ±4%.

The overall assessment of the UV absorbance data for lot A provides an estimate of the $\Delta A260$ value of 0.135 absorbance units with an RSD of 9.1%. Using this average absorbance value for lot A, the average viral particle concentration for lot A provided in Table 1, and a dilution factor of two, the 260 nm absorptivity ($\epsilon_{260}$) of this purified adenovirus preparation can be calculated to be 1.8×$10^{12}$ vp/ML-AU-cm. Given that this absorptivity value reflects the variability of both the protein concentration assay and the UV absorbance assay, propagation of error results in a final precision of 9.5% RSD for the estimate of adenovirus $\epsilon_{260}$. This absorptivity value, based on seven repeats of the protein concentration analysis and 26 independent determinations of the $AA_{260}$ value, provides a rigorous determination of the $\epsilon_{260}$ of a purified adenovirus preparation. Thus, one can determine viral particle concentration of similar adenovirus preparations using this $\epsilon_{260}$ value along with the simple, rugged analytical methodology described in this report.

Ten additional purified adenovirus preparations were analyzed for UV absorbance and protein concentration using the same methods as described for the analyses of lot A. Evaluation of different lots permitted both application of the newly derived $\epsilon_{260}$ value for calculation of viral particle concentrations, as well as demonstration that the relationship between viral particle concentration based on UV-absorbance analyses versus protein concentration analyses did not vary significantly from lot to lot. As an additional measure, the $A_{260}/A_{280}$ absorbance ratio was calculated for each virus preparation to assess the consistency of the relative purity of these preparations. These data are presented in Table 2.

Viral particle concentrations derived solely from protein concentration analyses do not incorporate the absorptivity factor and can thus be considered as "orthogonal" to the spectroscopic measurement. These data are presented in FIG. 2 as comparisons of the viral particle concentrations derived by UV absorbance relative to that derived from direct protein concentration analysis. The correlation between the two sets of results is extremely good, providing an $r^2$ value in excess of 0.999. This result confirms a very consistent nucleic acid to protein ratio in these virus preparations. Additionally, the fact that the slope of the regression line for the modified UV assay is very close to 1.0 supports that the $\epsilon_{260}$ value derived here ($1.8 \times 10^{12}$ vp/mL-AU-cm) will permit determination of viral particle concentrations from UV absorbance data that are in fairly precise agreement with those derived from more laborious protein concentration estimates. Moreover, the results from both of these methods correlate well with viral particle concentrations derived from another "orthogonal" method, quantitative polymerase chain reaction (QPCR) analyses, which quantitates the viral DNA content of purified adenovirus preparations.

Figure 2:
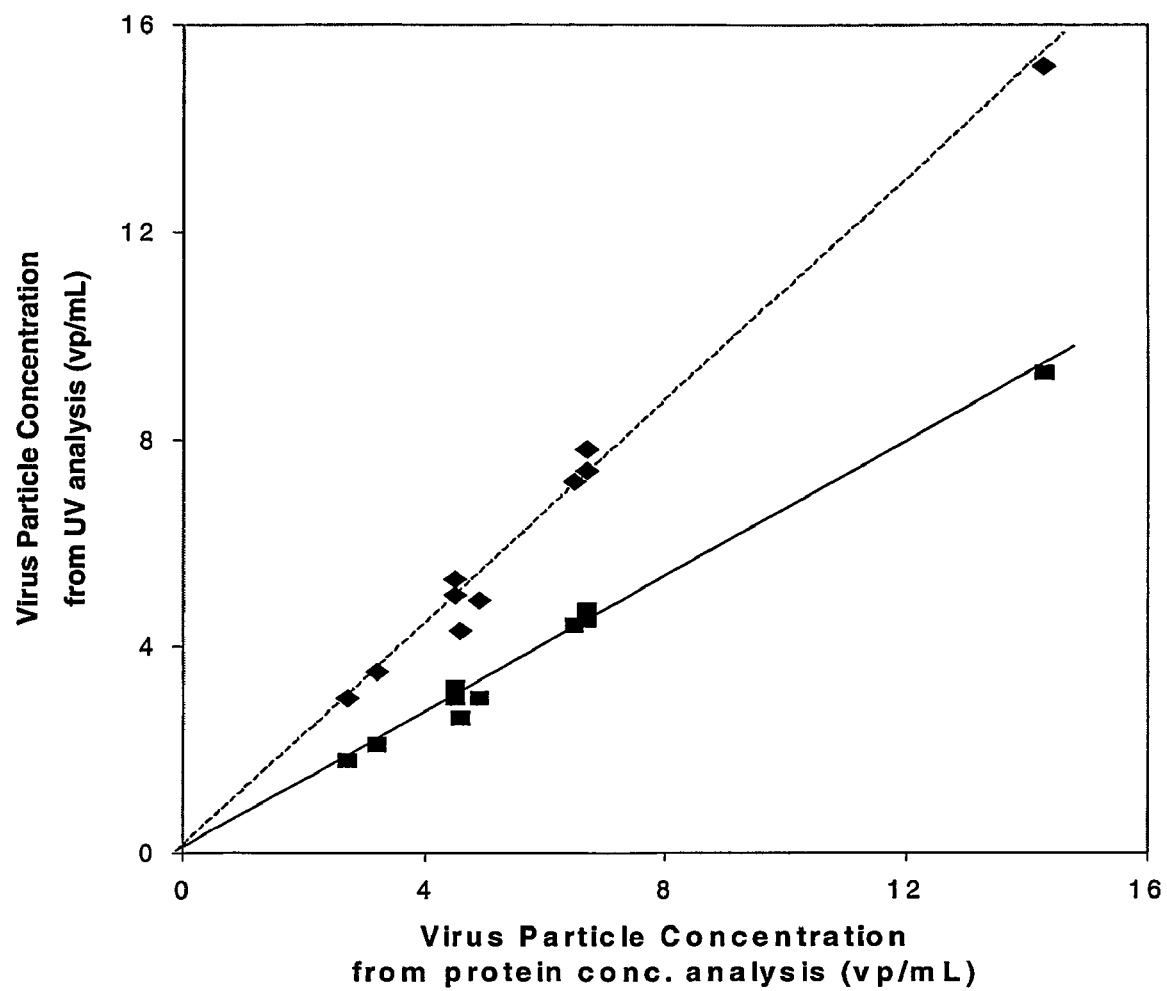
FIG. 2 shows the correlation plot of viral particle concentration data for ten different adenovirus preparations as determined from the UV-absorbance analysis versus from the direct protein analysis. Data for UV-absorbance derived virus particle concentration is shown for application of both the $\epsilon_{260}$ value derived herein (♦) and using the $\epsilon_{260}$ value derived by Maizel (■).

Further, the advantage of the modified UV absorbance method with newly derived adenovirus 260 nm absorptivity ($\epsilon_{260}$) described here versus use of the absorptivity factor disclosed in Maizel et al. (1968, *Virology* 36, 115-125) becomes readily apparent when a similar comparative plot of UV-absorbance derived viral particle concentration (based on Maizel's factor) versus the viral particle concentration derived solely from protein concentration is examined (FIG. 2). As expected, the results using the Maizel factor differ significantly, with viral particle concentrations that are not only 40% lower than those derived using the $\epsilon_{260}$ value disclosed herein, but also exhibit a slope for the viral particle concentration correlation (i.e., UV-derived versus protein-derived) of far less than 1.0. This latter result supports that the methodology described herein results in a more accurate assessment of viral particle concentration.

Overall, the methodology defined in this study allowed determination of a 260 nm absorbance value for purified adenovirus preparations that could be used along with the newly derived 260 nm adenovirus absorptivity to directly determine viral particle concentration by means of simple, rugged analyses that produce results consistent with those derived independently from protein concentration analyses by classical methods (i.e. the method of Lowry). Application of this methodology and associated 260 nm absorptivity value as a general method for characterizing purified adenovirus preparations may provide the general utility seen over the past decade with the Maizel method, but with more accurate results and much improved inter-laboratory ruggedness.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method of determining the virus particle concentration of an adenovirus preparation from a UV absorbance measurement, which comprises:
   a) using a previously established absorptivity/extinction coefficient ($\epsilon_{260}$) for the respective serotype of the adenovirus preparation, wherein said $\epsilon_{260}$ is determined under conditions of disruption of adenoviral particles and complete disruption of adenovirus DNA conformation;
   b) measuring the $A_{260}$ of a sample from the adenovirus preparation which has been prepared under treatment conditions which result in complete disruption of adenoviral particles and complete disruption of adenovirus DNA conformation; and,
   c) determining adenoviral particle concentration of said adenoviral sample from the $\epsilon_{260}$ and $A_{260}$ measurements of step a) and step b).

2. The method of claim 1 wherein the adenovirus serotype is adenovirus 5.

3. The method of claim 1 wherein said previously established absorptivity/extinction coefficient ($\epsilon_{260}$) is calculated by:
   a') determining the viral particle concentration of a sample from a adenovirus preparation of said adenovirus serotype;
   b') treating an independent sample from said adenovirus preparation under conditions which result in complete disruption of adenoviral particles and complete disruption of adenovirus DNA conformation;
   c') determining the $A_{260}$ of the sample from step b'); and,
   d') calculating the $\epsilon_{260}$ from the viral particle concentration of step a'), the $A_{260}$ value of step c') and the $A_{260}$ value of a matrix blank.

4. The method of claim 1 wherein the treatment conditions for the sample of step b) comprises addition of sodium dodecyl sulfate (SDS) to said adenovirus preparation at a concentration which completely disrupts both adenovirus particles and adenovirus DNA conformation.

5. The method of claim 1 wherein the treatment conditions for the sample of step b) comprises addition of at least about 1% sodium dodecyl sulfate (SDS) followed by incubation at a temperature which results in a complete disruption of both adenovirus particles and adenovirus DNA conformation.

6. The method of claim 3 wherein the treatment conditions for the sample of step b') comprises addition of sodium dodecyl sulfate (SDS) to said adenovirus preparation at a concentration which completely disrupts both adenovirus particles and adenovirus DNA conformation.

7. The method of claim 3 wherein the treatment conditions for the sample of step b') comprises addition of at least about 1% sodium dodecyl sulfate (SDS) followed by incubation at a temperature which results in a complete disruption of both adenovirus particles and adenovirus DNA conformation.

8. The method of claim 6 wherein the adenovirus serotype is adenovirus 5.

9. The method of claim 7 wherein the adenovirus serotype is adenovirus 5.

* * * * *